US009545107B2

United States Patent
Singh et al.

(10) Patent No.: US 9,545,107 B2
(45) Date of Patent: Jan. 17, 2017

(54) *ALLIUM FISTULOSUM* LEAF AGGLUTININ RECOMBINANT PROTEIN, ITS ENCODING POLYNUCLEOTIDE, PRIMER AND PROCESS FOR PREPARATION THEREOF

(71) Applicant: Council of Scientific and Industrial Research, New Delhi (IN)

(72) Inventors: Pradhyumna Kumar Singh, Lucknow (IN); Preeti Rai, Lucknow (IN); Rahul Singh, Lucknow (IN); Santosh Kumar Upadhyay, Lucknow (IN); Sharad Saurabh, Lucknow (IN); Harpal Singh, Lucknow (IN); Praveen Chandra Verma, Lucknow (IN); Chandrashekar Krishnappa, Lucknow (IN); Rakesh Tuli, Mohali (IN)

(73) Assignee: Council of Scientific and Industrial Research, New Dehli (IN)

( * ) Notice: Subject to any disclaimer, the term of this patent is extended or adjusted under 35 U.S.C. 154(b) by 0 days.

(21) Appl. No.: 14/368,443

(22) PCT Filed: Dec. 17, 2012

(86) PCT No.: PCT/IN2012/000822
§ 371 (c)(1),
(2) Date: Jun. 24, 2014

(87) PCT Pub. No.: WO2013/098852
PCT Pub. Date: Jul. 4, 2013

(65) Prior Publication Data
US 2015/0073126 A1 Mar. 12, 2015

(30) Foreign Application Priority Data
Dec. 28, 2011 (IN) .......................... 3850/DEL/2011

(51) Int. Cl.
| | |
|---|---|
| *A01N 37/46* | (2006.01) |
| *C07K 14/42* | (2006.01) |
| *A01N 47/44* | (2006.01) |
| *C12Q 1/68* | (2006.01) |
| *A01N 63/02* | (2006.01) |

(52) U.S. Cl.
CPC ............. *A01N 47/44* (2013.01); *A01N 37/46* (2013.01); *A01N 63/02* (2013.01); *C07K 14/42* (2013.01); *C12Q 1/6895* (2013.01)

(58) Field of Classification Search
CPC ........ A01N 37/46; C07K 14/42; C12Q 1/6895
See application file for complete search history.

(56) References Cited

U.S. PATENT DOCUMENTS

| | | |
|---|---|---|
| 5,407,454 A | 4/1995 | Cavalieri et al. |
| 5,545,820 A | 8/1996 | Gatehouse et al. |
| 6,127,532 A | 10/2000 | Raikhel et al. |

FOREIGN PATENT DOCUMENTS

| | | |
|---|---|---|
| WO | WO-9202139 A1 | 2/1992 |
| WO | WO-2013098852 A2 | 7/2013 |

OTHER PUBLICATIONS

Mizutani et al. 1980; Studies on agglutinability of various phytohemagglutinins for red blood cells of pigeons. Japanese J. Zootechnical Sciences. 51(7): 463-470, translation provided.*
"International Application Serial No. PCT/IN2012/000822, Article 19 Amendment filed Sep. 30, 2013 in response to the International Search Report and Written Opinion mailed Jul. 29, 2013", 3 pgs.
"International Application Serial No. PCT/IN2012/000822, International Preliminary Report on Patentability mailed Jul. 10, 2014", 7 pgs.
"International Application Serial No. PCT/IN2012/000822, Written Opinion mailed Jul. 29, 2013", 5 pgs.
Bandyopadhyay, Santanu, et al., "Binding of garlic (*Allium satium*) leaf lectin to the gut receptors of homopteran pests is correlated to its insecticidal activity", Plant Science, 161, (2001), 1025-1033.
Harper, M. S., et al., "Effect of wheat germ agglutinin on formation and structure of the peritrophic membrane in European corn borer (*Ostrinia nubilalis*) larvae", Tissue & Cell, 30(2), (1998), 166-176.
Hossain, Munshi, A., et al., "Transgenic Expression of Onion Leaf Lectin Gene in Indian Mustard Offers Protection against Aphid Colonization", Crop Science, 46, (2006), 2022-2032.
Murdock, Larry L., et al., "Lectins and Protease inhibitors as Plant Defenses against Insects", J. Agric. Food Chem., 50, (2002), 6605-6611.
Powell, Kevin S., et al., "Immunohistochemical and developmental studies to elucidate the mechanism of action of the snowdrop lectin on the rice brown planthopper, *Nilaparvata lugens* (Stal).", Journal of Insect Physiology, 44, (1998), 529-539.
Sadeghi, Amin, et al., "Ectopically expressed leaf and bulb lectins from garlic (*Allium sativum* L.) protect transgenic tobacco plants against cotton leafworm (*Spodoptera littoralis*)", Transgenic Res, 17, (2008), 9-18.
Saha, Prasenjit, et al., "A novel approach for developing resistance in rice against phloem limited viruses by antagonizing the phloem feeding hemipteran vectors", Plant Mol Biol, 62, (2006), 735-752.
Sauvion, Nicolas, et al., "Binding of the insecticidal lectin Concanavalin A in pea aphid, *Acyrthosiphon pisum* (Harris) and induced effects on the structure of midgut epithelial cells", Journal of Insect Physiology, 50, (2004), 1137-1150.

(Continued)

*Primary Examiner* — Karen Cochrane Carlson
(74) *Attorney, Agent, or Firm* — Schwegman Lundberg & Woessner, P.A.

(57) ABSTRACT

Nucleic acid sequence encoding *Allium fistulosum* leaf agglutinin (AFAL) is disclosed. The invention provides *Allium fistulosum* leaf agglutinin (AFAL) recombinant protein, its encoding nucleotides, primers and the process of preparation thereof, said recombinant protein is useful for insect control and haemagglutination activity. AFAL is found more toxic to sap sucking insect pest *Aphis gossypii* (cotton aphid) and *Bemisia tabaci* (whiteflies) as compared to known *Allium sativum* leaf agglutinin. AFAL can be used in the development of transgenic plants for resistance against sap sucking and chewing pests.

7 Claims, 4 Drawing Sheets

(56) References Cited

OTHER PUBLICATIONS

Smeets, Koen, et al., "Isolation, characterization and molecular cloning of a leaf-specific lectin from ramsons (*Allium ursinum* L.).", *Plant Molecular Biology*, 35, (1997), 531-535.

Smeets, Koen, "Isolation, characterization and molecular cloning of the mannose-binding lectins from leaves and roots of garlic (*Allium sativum* L.)", *Plant Molecular Biology*, 33, (1997), 223-234.

Van Damme, Els J.M., et al., "Cytoplasmic/nuclear plant lectins: a new story". *TRENDS in Plant Science*, 9(10), (Oct. 2004), 484-489.

Van Damme, Els J. M., et al., "Plant Lectins: A Composite of Several Distinct Families of Structurally and Evolutionary Related Proteins with Diverse Biological Roles", *Critical Reviews in Plant Sciences*, 17(6), (1998), 575-692.

Van Damme, Els J. M., et al., "The closely related homomeric and heterodimeric mannose-binding lectins from garlic are encoded by one-domain and two-domain lectin genes, respectively", *European Journal of Biochemistry*, 206(2), (Jun. 1992), 413-420.

"International Application Serial No. PCT/IN2012/000822, International Search Report mailed Jul. 29, 2013", 4 pgs.

Upadhyay, S. K, et al., "Purification and characterization of a lectin with high hemagglutination property isolated from Allium altaicum.", Protein Journal, 30(6), (Aug. 2011), 374-383.

Van Damme, Els J. M., et al., "Cloning and characterization of the lectin cDNA clones from onion, shallot and leek", Plant Molecular Biology, 23, (1993), 365-376.

\* cited by examiner

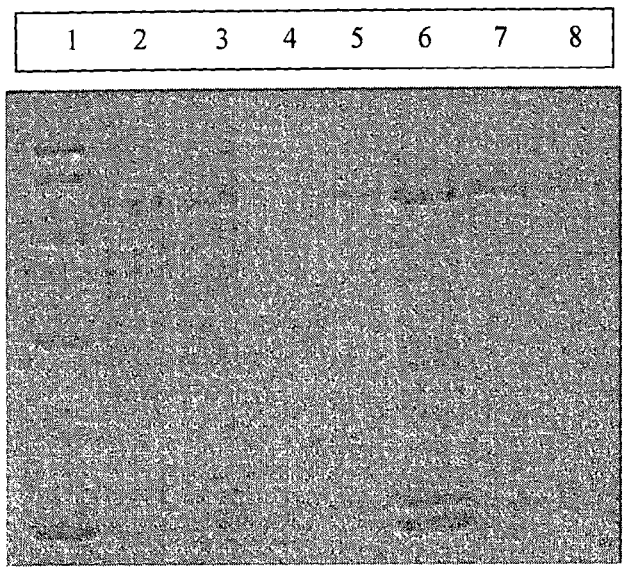
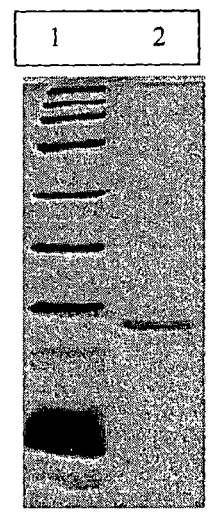
Fig. 1A               Fig. 1B
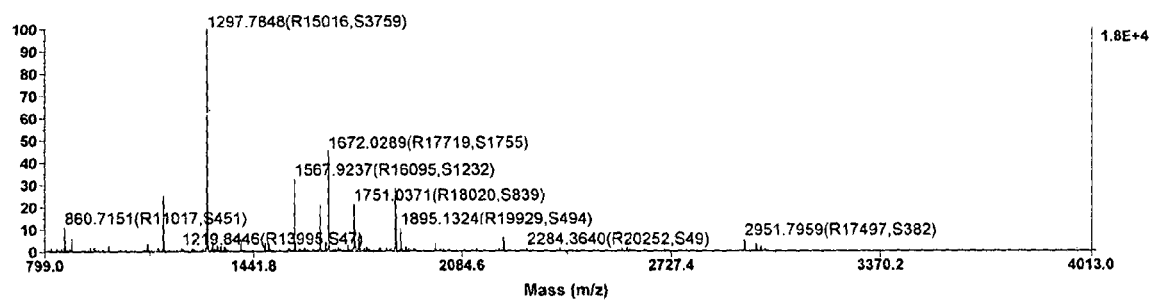
Fig. 2.

```
ATA     --MAYSVTCKLIMVCTVGAILSVLTATCMGRNILLNGEGLYAGQSLEEGPYRLAMDDCN  58
AUA     --MAISVNCKIIMVCAVGTILSILTPTSMGRNILLNGEGLYAGQSLEEGSYKLMDDCN   58
ASA     -------------------------------RNILTNDEGLYAGQSLDVNPYHLMEDCN  30
ASAL    MGRTTSSPKAMMRIATVAAILTILASTCMARNVLTNGEGLYAGQSLDVEQYKFMDDCN   60
AMPL    MGRTTPSPKLIMSITTVAAILTILASTCMARNLLTNGEGLYAGQSLDVEQYKFMDDCN   60
ACA     ---------------TVATILTILASTCMARNVLVNNEGLYAGQSLVVEQYTFMDDCN   45
AFAL    --MDSTPSPKLMSMTTVATILTILASTCMARNVLVNNEGLYAGQSLVVEQYTFMDDCN   58
                                       **:*  *.*********    *  : **:***

ATA     LVLYDEYSRPVWASNTGVTGRNGCRAVMQADGNFVVYDSNSRAVWASNSRKGNGNYILVL  118
AUA     LVLF-EYSTQVWASNTGVSGRNGCRAVMQADGNFVVYDSNSRAVWASQSRRGNGNYILAL  117
ASA     LVLY-DHSTAVWSSNTDIPGKKGCKAVMQSDGNFVVYDAEGASLWASHSVRGNGNYVLVL  89
ASAL    LVLY-EYSTPIWASNTGVTGKNGCRAVMQRDGNFVVYDVNGRPVWASNSVRGNGNYILVL  119
AMPL    LVLY-EYSTPIWASNTGVTGKNGCRAVMQKDGNFVVYDVNGRPVWATNSVRGNGNYILVL  119
ACA     LVLY-EYSTPIWASNTGVTGKNGCRAVMQADGNFVVYDVKGRAVWASNSRRGNGNYILVL  104
AFAL    LVLY-EYCAPIWASNTGVTGKNGCRAVMQADGNFVVYDVNGRAVWASNSRRGNGNYILVL  117
        ***: ::.    :*:***.:.*::**:**:* *********  :. .:**::* :*****:*.*

ATA     QKDRNAVIYGSDIWSTGTYRRGVG--------------GSVVTAMNGTVDAGFAVKNVTT  164
AUA     QEDRNVVIYGTDIWSTGTYRRGVG--------------GTVVTVINGTVDAGSGMENVTA  163
ASA     QEDGNVVIYGSDIWSTNTYK----------------------------------------  109
ASAL    QKDRNVVIYGSDIWSTGTYRRSVG--------------GAVVMAMNGTVDGGSVIGPVVV  165
AMPL    QQDRNVVIYGSDIWSTGTYRRSAG--------------GPVVMAMNGTVNGGSVVGPVIV  165
ACA     QKDRNVVIYGSDIWSTGTYRKKVG--------------GTVVMAMNGTVDGGSVVGPVTV  150
AFAL    QEDRNVVIYGSDIWSTGTYRRGPGPGPGAACKCDDDGPDIRSATLTGTVDLGSCNEGWEK  177
        *:*  *.****:*****.**:

ATA     AAVGDVAIA--------- 173
AUA     TAA-------------- 166
ASA     ------------------
ASAL    NQNVTAAIRKVGTGAA-- 181
AMPL    NQNVT-AIRKVGTSAA-- 180
ACA     NQNVT-AVRKVAAAA--- 164
AFAL    CASFYTILADCCRRPRG- 194
```

Fig. 4.

ALLIUM FISTULOSUM LEAF AGGLUTININ RECOMBINANT PROTEIN, ITS ENCODING POLYNUCLEOTIDE, PRIMER AND PROCESS FOR PREPARATION THEREOF

PRIORITY APPLICATIONS

This application is a U.S. National Stage Filing under 35 U.S.C. 371 from International Application No. PCT/IN2012/000822, filed on 17 Dec. 2012, and published as WO2013098852 on 4 Jul. 2013, which claims the benefit to Indian Application No. 3850/DEL/2011, filed on 28 Dec. 2011; which applications and publication are incorporated herein by reference in their entirety.

FIELD OF THE INVENTION

The invention relates to *Allium fistulosum* leaf agglutinin (AFAL) recombinant protein, its encoding polynucleotide, primers and process of preparation thereof said *Allium fistulosum* leaf agglutinin (AFAL) protein is useful for insecticidal activity and haemagglutination activity. In particular the present invention relates to nucleic acid sequence (afal) encoding for *Allium fistulosum* leaf agglutinin (AFAL) applicable for haemagglutination and insect control.

BACKGROUND AND PRIOR ART OF THE INVENTION

Plant lectins, also known as "agglutinins", are heterogeneous group of carbohydrate binding proteins, which are able to bind simple sugars and/or complex carbohydrates reversibly (Van Damme et al. 1998; *CRC Crit Rev Plant Sci* 17:575-692). They show a marked heterogeneity with respect to their molecular structures, sugar binding specificity and temporal and spatial regulation. Mannose binding lectins are widely found in higher plants and play a significant role in defense due to their ability to recognize high-Mannose-type glycans of microbial pathogens and plant predators (Van Damme et al. 1998, 1998, *CRC Grit Rev Plant Sci* 17:575-692; Van Damme et al. 2004 *Trends Plant Sci* 9:484-9). Mannose binding lectin from garlic leaf [*Allium sativum* leaf agglutinin (ASAL)] is a 25 kDa homodimeric protein, structurally and evolutionarily related to *Galanthus nivalis* agglutinin (GNA) (Smeets et al. 1997a, *Plant Mol Biol* 35: 531-535; Van Damme et al. 1992, *Eur J Biochem* 206:413-420). Some of the biological properties of ASAL are—(1) it readily agglutinates rabbit erythrocytes but does not affect human erythrocytes (Bandhopadhyay et. al. 2001, *Plant Sci.* 161:1025-1033; Smeets et al. 1997a, *Plant Mol Biol* 35: 531-535), (2) it has inhibitory effect against retrovirus (HIV1 and HIV2) induced cytopathicity in MT-4 cells (Smeets et. al. 1997b, *Plant Mol Biol* 33:223-234) and (3) it is toxic (growth inhibitory) against a spectrum of insects of order Homoptera, Lepidoptera and Coleoptera. Some important pests inhibited by ASAL are aphids [mustard aphid, peach potato aphid, tobacco aphid (Bandhopadhyay et al. 2001, *Plant Mol Biol* 33:223-234 Hossain et al. 2006, *Crop Sci* 46:2022-2032; Smeets et al. 1997a, *Plant Mol Biol* 35: 531-535), red cotton bug (Bandhopadhyay et al. 2001, *Plant. Mol. Biol.* 33:223-234), brown plant hopper, green leaf hopper (Saha et al. 2006, *Plant Mol. Biol.* 62:735-52) and cotton leaf worm (Sadeghi et al. 2008, *Transgenic Res.* 17:9-18). Although exact mechanism of insecticidal action of lectins is still not well understood, three different modes of action have been proposed—(1) binding of the lectins to the peritrophic matrix of the midgut, inhibiting nutrient absorption (Harper et al 1998, *Tissue Cell* 30: 166-176), (2) binding to glycoproteins on epithelial cells of the midgut and disrupting tissue integrity (Powell et al. 1998, *J Insect Physiol.* 44: 529-539; Sauvion et al. 2004, *J Insect Physiol.* 50: 1137-1150) and (3) binding to carbohydrate moieties of the sensory receptors of insect mouth parts, disrupting membrane integrity and interfering in the food detection ability of insects (Murdock et al. 2002, *J Agric Food Chem.* 50: 6605-6611). All these mechanisms result in decreased ability of insect to ingest food or absorb nutrients, leading to delayed development and premature death.

U.S. Pat. No. 5,545,820 (Gatehouse, et al., 1996) discloses the use of lectins having specific mannose-binding ability, derived from family Amaryllidaceae or Alliaceae for the control of insect pests. WO/1992/002139 relates to the use of lectins having specific mannose-binding ability, derived from family Amaryllidaceae or Alliaceae for the control of insect pests and the development of transgenic plants expressing such lectins. U.S. Pat. No. 5,407,454 relates to selected plant lectins having larvicidal activity against a number of common insect pests of agricultural crops. Insect resistance in the transgenic plants is due to insertion of larvicidal lectin gene in all the cells of the plants.

U.S. Pat. No. 6,127,532 (Raikhel) refers to transgenic plants containing cDNA encoding Gramineae lectin. Such transgenic plants expressed barley lectin and stored in in the leaves. The transgenic plants, particularly the leaves exhibit insecticidal and fungicidal' properties.

*Allium fistulosum*

*Allium fistulosum* L. (Welsh onion, Japanese bunching onion) is a perennial onion. Other names that may apply to this plant include green onion, spring onion, escallion, and salad onion. These names are ambiguous, as they may also be used to refer to any young green onion stalk, whether grown from Welsh onions, common bulb onions, or other similar members of the genus *Allium*. The species is very similar in taste and odor to the related bulb onion, *Allium cepa*, and hybrids between the two (tree onions). The Welsh onion, however, does not develop bulbs, and possesses hollow leaves ("*fistulosum*" means "hollow") and scapes. Large varieties of the Welsh onion resemble the leek, such as the Japanese 'negi', whilst smaller varieties resemble chives. Many Welsh onions can be multiplied by forming perennial evergreen clumps. Next to culinary use, it is also grown as an ornamental plant. Historically, the Welsh onion was known as the cibol.

The name "Welsh onion" has become a misnomer in modern English, as *Allium fistulosum* is not indigenous to Wales. "Welsh" preserves the original meaning of the Old English word "welisc", or Old German "welsche", meaning "foreign" (compare wal- in "walnut", of the same etymological origin). The species originated in Asia, possibly Siberia or China.

Culinary Use

In the West, the Welsh onion is primarily used as a scallion or salad onion, but is widely used in other parts of the world, particularly East Asia.

Russia: Welsh onion is used in Russia in the spring for adding green leaves to salads.

Asia: The Welsh onion is an ingredient in Asian cuisine, especially in East and Southeast Asia. It is particularly important in China, Japan, and Korea, hence the other English name for this plant, 'Japanese bunching onion'. Bulb onions were introduced to East Asia in the 19th century, but *A. fistulosum* remains more popular and widespread. In Japan, it is used in miso soup, negimaki (beef and scallion rolls), among others, and it is widely sliced up and used as a garnish on teriyaki or takoyaki.

Jamaica: Known as escallion, the Welsh onion is an ingredient in Jamaican cuisine, in combination with thyme, scotch bonnet pepper, garlic and allspice (called pimenta). Recipes with escallion sometimes suggest leek as a substitute in salads. Jamaican dried spice mixtures using escallion are available commercially. The Jamaican name is probably a variant of scallion, the term used loosely for the spring onion and various other plants in the genus *Allium*.

Lacking in the Prior Art

*Allium* lectin disclosed in present invention shows high insecticidal activity and therefore novel. Homology of the nucleotide sequence with available nucleotide sequences in database shows more than 90% homology.

OBJECTIVES OF THE INVENTION a) The main objective of the invention is to provide nucleic acid sequence which encodes for *Allium fistulosum* leaf agglutinin b) Another objective of the present invention is to provide gene specific primers

```
                                          SEQ ID NO: 5
    GSP 1 (5'-ATGGACAGTACTCCATCTCCTAAAC-3');
    and
                                          SEQ ID NO: 6
    GSP 2 (5'-TTAGCCCCTTGGCCTCCTGCA-3'),
``` useful for amplification of the gene.

c) Another objective of the present invention is to provide agglutinin recombinant protein having high insecticidal activity d) Another objective of the present invention is the application of *Allium fistulosum* leaf agglutinin protein for insect control.

SUMMARY OF THE INVENTION

Accordingly, the present invention relates to *Allium fistulosum* leaf agglutinin (AFAL) recombinant protein, its encoding nucleotides, primers and the process of preparation thereof, said protein is useful for insect control and haemagglutination activity.

In an embodiment of present invention, the process of preparation of *Allium fistulosum* leaf agglutinin (afal) recombinant protein, useful for insecticidal activity and haemagglutination activity, comprising of following steps— a) Extracting of total RNA from the *Allium fistulosum* leaves b) Synthesizing of cDNA from total RNA extracted from leaves of *Allium fistulosum* c) Designing of primers GSP1 and GSP2 from 5'- and 3'-RACE fragment of c DNA to clone full-length protein encoding DNA, designing of primers GSP3 and GSP4 for cloning of the DNA encoding mature polypeptide of AFAL protein, d) Expressing the DNA encoding the mature AFAL in *E. coli* SUMO expression vector where SUMO peptide is fused with AFAL at the N-terminus and expressed in *E. coli* under T7 promoter to get desired AFAL recombinant protein.

In another embodiment of the present invention the primers GSP1 and GSP2 comprise:

1. GSP1 represented by SEQ ID NO:5, and
2. GSP2 represented by SEQ ID NO:6.

*Allium fistulosum* leaf agglutinin (AFAL) recombinant protein is 8-10 fold more toxic to cotton aphid (*Aphis gossypii*) and 6-8 fold to whiteflies (*Bemisia tabaci*) as compared to well-known *Allium sativum* leaf agglutinin.

According to the invention a DNA fragment of 651 bp was cloned from total cDNA of *A. fistulosum* leaves, consisted of, 585 bp long open reading frame encoding AFAL precursor protein of 194 amino acid residues with 28 amino acid long N-terminal signal peptide and 56 amino acid long C-terminal peptide. The amino acid sequences of AFAL are different from the other reported *Allium* lectin sequences. The cloned genomic DNA sequence of afal showed absence of intron.

In another embodiment of the present invention the nucleic acid sequence having SEQ ID NO:2, encodes a polypeptide as represented in SEQ ID NO:4, which is a 110 amino acid residue long mature peptide of *Allium fistulosum* leaf agglutinin(AFAL), having a molecular weight of ~12 kDa.

In yet another embodiment of the present invention the polypeptide has the minimum haemagglutination value of in the range of 6-10 ng/ml.

In yet another embodiment of the present invention the polypeptide exhibits insecticidal activity selected from the group comprising haemagglutination, insecticidal, antifungal and anti-prolific activity.

In still yet another embodiment of the present invention the polypeptide exhibits haemagglutination activity selected from the group comprising haemagglutination, insecticidal, antifungal and anti-prolific activity.

BRIEF DESCRIPTION OF FIGURES

FIG. 1A. Lane 1, Molecular weight markers; Lane 2, Total soluble protein from leaves of *A. fistulosum*; Lane 3, Unbound total soluble protein; Lane 4, Column wash (before elution); Lanes 5-8, eluted fractions. FIG. 1B. Lane 1, Molecular weight markers; Lane 2, Purified AFAL concentrated on 10 kDa cut-off filtration device.

FIG. 2. Peptide mass fingerprinting of AFAL

DETAILED DESCRIPTION OF THE INVENTION

Figure 3:
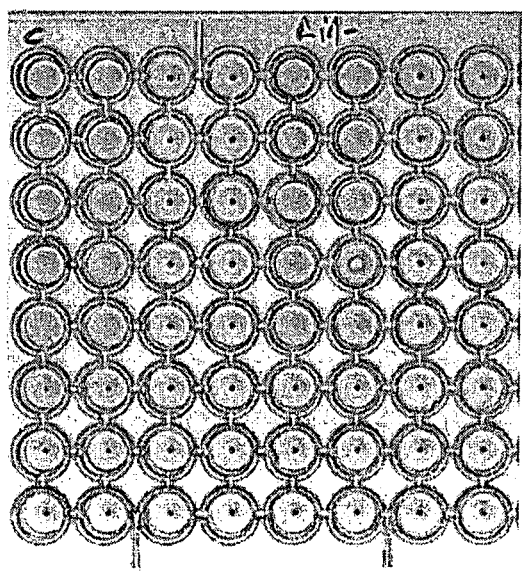
FIG. 3. V-bottom plate showing haemagglutination of rabbit erythrocytes by AFAL FIG. 4 Clustalw analysis of AFAL with other *Allium lectins*. Amino acid identity of AFAL with other mannose binding lectins vary from 67% to 75%. Dark area represents mannose binding domain. (SEQ ID NOs: 3 and 12-17).

The leaves of *Allium fistulosum* were collected from the National Bureau of Plant Genetic Resources, Bhowali, Nainital, Uttarakhand, India, and used for the purification of *Allium fistulosum* leaf agglutinin (AFAL). It was purified on mannose-agarose affinity column, followed by cut-off filtration device (Example 1, FIGS. 1 & 2). The purified protein was used for brief characterization.

AFAL shows several times better insecticidal activity against sap sucking pest *Aphis gossypii* (cotton aphids), *Bemisia tabaci* (whitefly) as compared to ASAL (Example 3). Large amount of purified protein is required for further characterization. The purification of AFAL from plant leaves in bulk amount is difficult due to unavailability of plant material and very low accumulation of the lectin in leaves. Expression of protein in a re combinant system is an alternative approach to produce the desired protein in large amount, which required the cloning of AFAL encoding gene. The gene (afal) was cloned from cDNA prepared from total RNA of leaves of *A. fistulosum*. The cloning was done by RACE (Rapid Amplification of cDNA Ends) using degenerate primers designed from the conserved mannose binding domain.

The cloned DNA fragment gene was of 651 bp, consisted of 585 bp open reading frame, 66 bp 5' untranslated leader sequence. The full-length gene encoding AFAL precursor protein of 194 amino acid residues had 28 amino acid long N-terminal signal and 56 amino acid long C-terminal peptide. It contains three mannose binding domains as reported in the case of other mannose binding lectins (Example 5). The cloned genomic DNA sequence of afal had no intron. The amino acid sequences of AFAL are different from the other reported *Allium* lectin sequences (Example 5, FIG. 4).

The gene encoding insecticidal protein was cloned in *E. coli* expression vector in fusion with SUMO peptide and the recombinant insecticidal protein was expressed. The protein was purified on Ni-NTA column. The recombinant protein showed the insecticidal activity against cotton aphids and whiteflies. The gene encoding the mature peptide was cloned in plant expression vector pBI121 under CaMVE35S promoter (Example 6-8).

In the embodiment of the invention, the cloned full-length gene sequence of *Allium fistulosum* leaf agglutinin (afal) similar to SEQ ID NO:1. SEQ ID NO:1 contains DNA sequence which encodes N-terminal signal peptide, mature peptide and C-terminal peptide.

In another embodiment of the invention, nucleotides encoding N-terminal signal peptide and C-terminal peptide are removed from SEQ ID NO:1, to obtain the mature protein encoding gene sequence, similar to SEQ ID NO:2.

In another embodiment of the invention, the gene sequence of SEQ ID NO:1 was translated to obtain the full-length amino acid sequences of AFAL similar to SEQ ID NO:3.

In yet another embodiment of the invention, the gene sequence of SEQ ID NO:2 was translated to obtain mature AFAL with amino acid sequence similar to SEQ ID NO:4.

In yet another embodiment of the invention, the gene encoding the mature AFAL is cloned in *E. coli* SUMO expression vector where SUMO peptide is fused with AFAL at the N-terminus and expressed in *E. coli* under T7 promoter.

In yet another embodiment of the invention, the AFAL agglutinated rabbit erythrocytes.

In yet another embodiment of the invention, the AFAL was tested against insect pests like cotton aphid (*Aphis gossypii*) and whiteflies (*Bemisia tabaci*).

In yet another embodiment of the invention, the gene encoding the mature AFAL was cloned in plant expression vector under constitutive promoter CaMV35S and phloem specific promoters CoYMoV, RSS1, RolC etc. and expressed in transgenic plants for insect control.

(5) Examples

Example 1

Isolation and Purification of the Protein

*Allium fistulosum* leaves were collected from National Bureau of Plant Genetic Resources, Regional Centre, Bhawali, Uttaranchal, India. The protein was purified according to the protocol described (Smeets et al., 1997b). The purified protein was further purified on 50 kDa cut-off filtration device. The purified protein was concentrated on 10 kDa cut-off filter and stabilized in PBS for experiments.

Example 2

Peptide Mass Finger Printing

The purified protein was resolved on SDS-PAGE. The protein band was excised and digested with trypsin and used for peptide mass finger printing. The data was analyzed on MASCOT search. The peptides were found matching to the mannose binding lectins (FIG. 2).

Example 3

Haemagglutination Assay

Haemagglutination assays with rabbit RBCs were carried out in V-bottomed microtitre plates. Total volume of assay was 100 µl, 50 µl aliquot of two-fold serially diluted lectin in PBS was mixed with 50 µl 1 of 2% trypsinized rabbit erythrocytes suspension. Microtitre plate was incubated for 1 hour at room temperature. Agglutination was assessed visually. Reciprocal of the highest dilution of lectin showing detectable agglutination was taken as titer of the haemagglutination

TABLE 1

Haemagglutination assay of AFAL and its comparision with ASAL

| S.N | Agglutinin | Haemagglutination |
|---|---|---|
| 1 | *Allium sativum* agglutinin (standard) | 200 ng/ml |
| 2 | *Allium fistulosum* leaf agglutinin | 8 ng/ml |

Example 4

Insect Bioassay

Insect bioassay was carried out against sap sucking pest, cotton aphid (*Aphis gossypii*) and whiteflies (*Bemisia tabaci*). The known amount of purified protein was mixed in synthetic diet and insect mortality data was recorded at different time interval. The data was used for the calculation of $LC_{50}$ using probit analysis.

TABLE 2

Insecticidal activity of AFAL purified from leaves of *A. fistulosum*.

| S.N | Agglutinin | Aphids (*Aphis gossypii*), LC$_{50}$ | Whiteflies (*Bemisia tabaci*), LC$_{50}$ |
|---|---|---|---|
| 1 | *Allium sativum* agglutinin (Standard) | 68 μg/ml | 76 μg/ml |
| 2 | *Galanthus nivalis* agglutinin | 51.39 μg/ml | 53.39 μg/ml |
| 3 | *Allium fistulosum* agglutinin | 7.1 μg/ml | 8.5 μg/ml |

Example 5

Gene Cloning and Characterization cDNA was synthesized following standard protocol. The 3' RACE was performed with degenerate primer {5'ATGCA(A/G)(C/G)A (G/T)GACTGCAACC-3'; SEQ ID NO:11} (primer sequence was derived from the mannose-binding site, QXDXNXVXY (SEQ ID NO:10), conserved among most of the monocot mannose-binding lectins) and universal primer. For 5' RACE, RNA was reversely transcribed with the 5'-RACE CDS Primer. Based on the 3' and 5' RACE results, primers were designed for amplification of full length gene, GSP1 (5'-ATGGACAGTACTCCATCTC-CTAAAC-3'; SEQ ID NO:5) GSP2 (5'- GCCCCTTGGC-CTCCTGCA-3'; SEQ ID NO:9). The full-length gene was amplified and cloned. The mature AFAL encoding DNA was amplified with primers

```
                                       SEQ ID NO: 7
    GSP 3 (5'-AGAAACGTATTGGTGAACAACG-3');
    and

SEQ ID NO: 8
    GSP 4 (5'-TTATCTTCTGTAGGTACCAGTAGAC-3').
```

The amino acid sequence of AFAL was deduced with Expasy translate tool. The analysis and comparison of the deduced amino acid sequences and nucleotide sequences obtained in RACE was performed with blast p (Standard Protein-Protein BLAST), blastn (Standard Nucleotide-Nucleotide BLAST) on NCBI (www.ncbi.nlm.nih.gov) and clustal W.

SEQ ID NO:1 Nucleic acid sequences encoding full-length AFAL
SEQ ID NO:2 Nucleic acid sequences encoding mature AFAL.
SEQ ID NO:3 Amino acid sequence of the *Allium fistulosum* leaf agglutinin
SEQ ID NO:4 Amino acid sequence of the mature *Allium fistulosum* leaf agglutinin

```
Nucleic acid sequences encoding full length AFAL
                                          SEQ ID NO: 1
ATGGACAGTA CTCCATCTCC TAAACTAATG AGCATGACCA       60
CTGTAGCCAC CATCCTAACC
ATTTTGGCAT CTACATGCAT GGCCAGAAAC GTATTGGTGA      120
ACAACGAAGG ACTGTACGCA
GGCCAATCCC TAGTCGTAGA ACAGTACACT TTTACAATGC      180
AGGATGACTG CAACCTTGTA
CTCTACGAAT ACTGCGCCCC AATCTGGGCC TCAAACACGG      240
GCGTCACCGG CAAAAATGGG
TGCAGGGCCG TGATGCAGGC TGATGGCAAC TTTGTGGTCT      300
ACGATGTTAA CGGGCGTGCC
GTCTGGGCCA GTAACAGCAG AAGAGGGAAC GGAAACTATA      360
TCCTGGTGCT TCAGGAGGAC
AGGAACGTTG TTATTTACGG ATCTGATATT TGGTCTACTG      420
GTACGTACAG AAGAGGGCCC
GGTCCTGGTC CTGGTGCCGC CTGCAAGTGC GATGACGATG      480
GTCCTGACAT TCGCAGTGCT
ACTTTGACAG GCACTGTCGA TTTGGGAAGC TGCAACGAGG      540
GATGGGAGAA GTGCGCATCT
TTCTACACCA TCCTCGCGGA TTGCTGCAGG AGGCCAAGGG      585
GCTAA Nucleic acid sequences encoding mature AFAL.
                                          SEQ ID NO: 2
AGAAACGTAT TGGTGAACAA CGAAGGACTG TACGCAGGCC       60
AATCCCTAGT CGTAGAACAG
TACACTTTTA CAATGCAGGA TGACTGCAAC CTTGTACTCT      120
ACGAATACTG CGCCCCAATC
TGGGCCTCAA ACACGGGCGT CACCGGCAAA AATGGGTGCA      180
GGGCCGTGAT GCAGGCTGAT
GGCAACTTTG TGGTCTACGA TGTTAACGGG CGTGCCGTCT      240
GGGCCAGTAA CAGCAGAAGA
GGGAACGCAA ACTATATCCT GGTGCTTCAG GAGGACAGGA      300
ACGTTGTTAT TTACGGATCT
GATATTGGT CTACTGGTAC GTACAGAAGA                  330

Amino acid sequence of AFAL
                                          SEQ ID NO: 3
MET ASP SER THR PRO SER PRO LYS LEU MET SER       20
MET THR THR VAL ALA THR ILE LEU THR
ILE LEU ALA SER THR CYS MET ALA ARG ASN VAL       40
LEU VAL ASN ASN GLU GLY LEU TYR ALA
GLY GLN SER LEU VAL VAL GLU GLN TYR THR PHE       60
THR MET GLN ASP ASP CYS ASN LEU VAL
LEU TYR GLU TYR CYS ALA PRO ILE TRP ALA SER       80
ASN THR GLY VAL THR GLY LYS ASN GLY
CYS ARG ALA VAL MET GLN ALA ASP GLY ASN PHE      100
VAL VAL TYR ASP VAL ASN GLY ARG ALA
VAL TRP ALA SER ASN SER ARG ARG GLY ASN GLY      120
ASN TYR ILE LEU VAL LEU GLN GLU ASP
ARG ASN VAL VAL ILE TYR GLY SER ASP ILE TRP      140
SER THR GLY THR TYR ARG ARG GLY PRO
GLY PRO GLY PRO GLY ALA ALA CYS LYS CYS ASP      160
ASP ASP GLY PRO ASP ILE ARG SER ALA
THR LEU THR GLY THR VAL ASP LEU GLY SER CYS      180
ASN GLU GLY TRP GLU LYS CYS ALA SER
PHE TYR THR ILE LEU ALA ASP CYS CYS ARG ARG      194
PRO ARG GLY Amino acid sequence of the mature AFAL
                                          SEQ ID NO: 4
ARG ASN VAL LEU VAL ASN ASN GLU GLY LEU TYR       20
ALA GLY GLN SER LEU VAL VAL GLU GLN
TYR THR PHE THR MET GLN ASP ASP CYS ASN LEU       40
VAL LEO TYR GLU TYR CYS ALA PRO ILE
TRP ALA SER ASN THR GLY VAL THR GLY LYS ASN       60
GLY CYS ARG ALA VAL MET GLN ALA ASP
GLY ASN PHE VAL VAL TYR ASP VAL ASN GLY ARG       80
ALA VAL TRP ALA SER ASN SER ARG ARG
GLY ASN GLY ASN TYR ILE LEU VAL LEU GLN GLU      100
ASP ARG ASN VAL VAL ILE TYR GLY SER
ASP ILE TRP SER THR GLY THR TYR ARG ARG          110

Primer sequence GSP1:
                                          SEQ ID NO: 5
(5'-ATGGACAGTACTCCATCTCCTAAAC-3').

Primer sequence GSP2:
                                          SEQ ID NO: 6
(5'-GCCCCTTGGCCTCCTGCA-3').

Primer sequence GSP3:
                                          SEQ ID NO: 7
(5'-AGAAACGTATTGGTGAACAACG-3').

Primer sequence GSP4:
                                          SEQ ID NO: 8
(5'-TTATCTTCTGTAGGTACCAGTAGAC-3')..
```

Example 6

Figure 5:
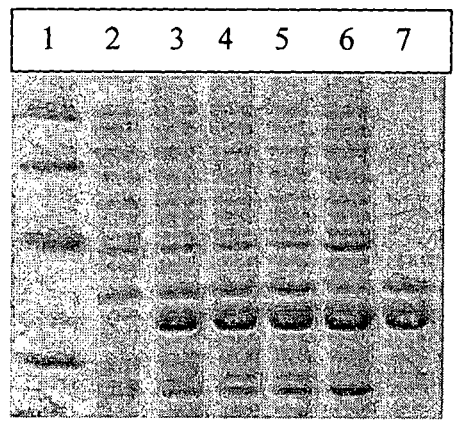
FIG. 5. Lane 1, Molecular weight markers; lane 2. uninduced bacterial lysate; lane 3-5, sample after 1 h, 2 h and 3 h induction; lane 6, supernatant of 3 hr induced culture; lane 7, protein in inclusion.

Expression of AFAL with N-Terminal Fusion of SUMO in *E. coli* and Purification of SUMO-AFAL The gene encoding mature AFAL was cloned in *E. coli* expression vector in fusion with SUMO peptide under T7 promoter. SUMO had (His$_6$) tag attached which helped in the purification of recombinantly expressed protein on Ni-NTA resin. SUMO-AFAL was expressed after induction with IPTG. The expression of the recombinant protein was observed every hour for 3 hours. After 3 hours of induction, cells were harvested by centrifugation; suspended in 20 mM TrisCl (pH 8). Bacterial cells were lysed by lysozymen and disrupted by sonication. The lysed bacterial cells were spun and supernatant and pellet were collected and electrophorased on denaturing PAGE (FIG. 5). Approximately half of the recombinant protein was in the soluble form and rest as inclusion in the pellet.

Purification of SUMO-AFAL from *E. coli*

Figure 6:
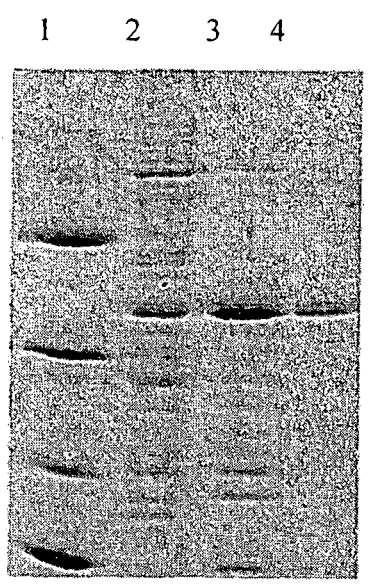
FIG. 6. Lane 1, molecular weight markers; lane 2, total *E. coli* protein containing SUMO-AFAL; lanes 3-4 represent purified fusion protein.

Recombinantly expressed SUMO-AFAL was purified on metal-affinity column. Total bacterial protein was loaded on Ni-column, pre-equilibrated with the buffer (20 mM Tris pH 8, 300 mM NaCl and 10 mM Imidazole). NaCl and Imidazole were used to prevent the binding of non-specific proteins to the column. The column was washed with same buffer having 20 mM imidazole to remove low affinity bound proteins. Finally, the protein was eluted with 200 mM Imidazole (FIG. 6).

Example 7

Insect Bioassay with Recombinant Fusion Protein

Insect bioassay was carried out against sap sucking pest, cotton aphid (*Aphis gossypii*) and whiteflies (*Bemisia tabaci*). The known amount of SUMO-AFAL was mixed in synthetic diet and insect mortality data was recorded at different time interval. The data was used for the calculation of LC$_{50}$ using probit analysis. SUMO-ASAL served as positive control. The results of insect bioassay is shown in the table 3

TABLE 3

| | LC$_{50}$ | |
|---|---|---|
| S.N Agglutinin | Aphids (*Aphis gossypii*) | Whiteflies (*Bemisia tabaci*) |
| 1 Recombinant ASAL (SUMO-ASAL) | 55.05 µg/ml | 51.2 µg/ml |
| 2 Recombinant AFAL (SUMO-AFAL) | 4.97 µg/ml | 8.80 µg/ml |

Advantages of the Invention

The lectin protein being disclosed in the present invention (AFAL) is 6-10 folds more toxic to insects like aphids and whiteflies as compared to the standard *Allium sativum* leaf lectin (ASAL). AFAL also showed 25 folds higher haemagglutination activity as compared to ASAL. AFAL binds to lesser number of carbohydrate residues on glycans array as compared to ASAL. This assures fewer non-specific binding of AFAL to carbohydrates and therefore expected to be safe as compared to ASAL.

REFERENCES CITED

| US patents | | |
|---|---|---|
| 5,545,820 | Aug. 13, 1996 | Gatehouse et al |
| 6,127,532 | Oct. 3, 2000 | Raikhel |
| WO/1992/002139 | Feb. 20, 1992 | Gatehouse et al |
| 5,407,454 | Apr. 18, 1995 | Anthony et al |

OTHER REFERENCES

Bandyopadhyay S, Roy A, Das S (2001) Binding of garlic (*Allium sativum*) leaf lectin to the gut receptors of homopteran pests is correlated to its insecticidal activity. Plant Sci 161:1025-1033

Harper S M, Hopkins T L, Czapala T H (1998) Effect of wheat germ agglutinin on formation and structure of the peritrophic membrane in European corn borer (*Ostrina nubilalis*) larvae. Tissue Cell 30: 166-176

Hossain M A, Maiti M K, Basu A, Sen S, Ghosh A K, Sen S K (2006) Transgenic Expression of Onion Leaf Lectin Gene in Indian Mustard Offers Protection against Aphid Colonization. Crop Sci 46:2022-2032

Murdock L L, Shade R E (2002) Lectins and protease inhibitors as plant defenses against insects. J Agric Food Chem 50: 6605-6611

Powell K S, Spence J, Bharathi M, Gatehouse J A, Gatehouse A M R (1998) Immunohistochemical and developmental studies to elucidate the mechanism of action of the snowdrop lectin on the rice brown planthopper *Nilaparvata lugens* (Stal). J Insect Physiol 44: 529-539

Sadeghi A, Smagghe G, Broeders S, Hernalsteens J P, De Greve H, Peumans W J, Van Damme E J (2008) Ectopically expressed leaf and bulb lectins from garlic (*Allium sativum* L.) protect transgenic tobacco plants against cotton leaf worm (*Spodoptera littoralis*). Transgenic Res 17:9-18

Saha P, Dasgupta I, Das S (2006) A novel approach for developing resistance in rice against phloem limited viruses by antagonizing the phloem feeding hemipteran vectors. Plant Mol Biol 62:735-52

Sauvion. N, Nardon C, Febvay G, Gatehouse A M R, Rahbe Y (2004) Binding of the insecticidal lectin concanavalin A in pea aphid, *Acyrthosiphon pisum* (Harris) and induced effects on the structure of midgut epithelial cells. J Insect Physiol 50: 1137-1150

Smeets K, Van Damme E J M, Van Leuven F, Peumans W J (1997 a) Isolation, characterization and molecular cloning of a leaf-specific lectin from ramsons (*Allium ursinum* L.). Plant Mol Biol 35: 531-535

Smeets K, Van Damme E J M, Verhaert P, Barre A, Rouge, P, Van Leuven F, Peumans W J (1997 b) Isolation, characterization and molecular cloning of the mannose-binding lectins from leaves and roots of garlic (*Allium sativum* L.). Plant Mol Biol 33:223-234

Van Damme E J, Barre A, Rougé P, Peumans W J (2004) Cytoplasmic/nuclear plant lectins: a new story. Trends Plant Sci 9:484-9

Van Damme E J M, Peumans W J, Barre A, Rouge' P (1998) Plant lectins: a composite of several distinct families of structurally and evolutionary related proteins with diverse biological roles. CRC Crit Rev Plant Sci 17:575-692

Van Damme E J M, Smeets K, Torrekens S, Van Leuven F, Goldstein I J, Peumans W J (1992) The closely related homomeric and heterodimeric mannose-binding lectins from garlic are encoded by one-domain and two-domain lectin genes, respectively. Eur J Biochem 206:413-420.

The invention claimed is:

1. A process for preparation of *Allium fistulosum* leaf agglutinin (AFAL) recombinant protein by amplifying the AFAL gene, wherein the process comprises:
   a) extracting total RNA from *Allium fistulosum* leaves;
   b) synthesizing cDNA from total RNA extracted from the leaves of *Allium fistulosum*;
   c) employing primers with a nucleotide sequence as set forth in SEQ ID NO:5 and SEQ ID NO:6 with cDNA of (b) to amplify and obtain a nucleotide fragment encoding full-length AFAL protein;
   d) employing primers having nucleotide sequences as set forth in SEQ ID NO:7 and SEQ ID NO:8 with said nucleotide fragment to amplify and obtain a polynucleotide fragment encoding mature AFAL protein;
   e) obtaining an expression cassette comprising said polynucleotide fragment and a promoter;
   f) introducing said expression cassette in a host to obtain recombinant host cells; and
   g) culturing said recombinant host cells to obtain recombinant AFAL protein.

2. Nucleic acid sequence represented by SEQ ID NO:1, obtained by the process claimed in claim 1, wherein SEQ ID NO:1 is comprised of 1 to 585 nucleotides or the sequence complementary thereto, which encodes full-length *Allium fistulosum* leaf agglutinin polypeptide, wherein nucleotide sequence 583 to 585 is a stop codon.

3. A cDNA fragment having a nucleic acid sequence as set forth in SEQ ID NO:2.

4. A method to express *Allium fistulosum* leaf agglutinin (AFAL) polypeptide, comprising: introducing to a cell genome a vector comprising a nucleotide sequence having SEQ ID NO:1 or SEQ ID NO:2 operably linked to a promoter expressed in *E. coli, Pseudomonas, Pichia pastoris* or *Saccharomyces cerevisiae*; and isolating from the cell a polypeptide having an amino acid sequence as set forth in SEQ ID NO:4, wherein the said polypeptide is a 110 amino acid residue long mature peptide of *Allium fistulosum* leaf agglutinin (AFAL) recombinant protein, having a molecular weight of about 12 kDa.

5. A method for making a plant resistant to insects, said method comprising producing an amount of isolated polypeptide having an amino acid sequence as set forth in SEQ ID NO: 4 in said plant, effective to exhibit insecticidal activity against the insect, wherein said plant is transformed with a nucleic acid having SEQ ID NO: 1.

6. The method as claimed in claim 5, wherein the isolated protein is in an amount that exhibits insecticidal activity against *Aphis gossypii, Bemisia tabaci, Helicoverpa armigera* and *Spodoptera litura*.

7. The method as claimed in claim 5, wherein the insect belongs to order lepidoptera, homoptera, coleopteran, or diptera.

* * * * *

SEQUENCE LISTING

<160> NUMBER OF SEQ ID NOS: 17

<210> SEQ ID NO 1
<211> LENGTH: 585
<212> TYPE: DNA
<213> ORGANISM: Allium Fistulosum

<400> SEQUENCE: 1

```
atggacagta ctccatctcc taaactaatg agcatgacca ctgtagccac catcctaacc     60
attttggcat ctacatgcat ggccagaaac gtattggtga acaacgaagg actgtacgca    120
ggccaatccc tagtcgtaga acagtacact tttacaatgc aggatgactg caaccttgta    180
ctctacgaat actgcgcccc aatctgggcc tcaaacacgg gcgtcaccgg caaaaatggg    240
tgcagggccg tgatgcaggc tgatggcaac tttgtggtct acgatgttaa cgggcgtgcc    300
gtctgggcca gtaacagcag aagagggaac ggaaactata tcctggtgct tcaggaggac    360
aggaacgttg ttatttacgg atctgatatt tggtctactg gtacgtacag aagagggccc    420
ggtcctggtc ctggtgccgc ctgcaagtgc gatgacgatg tcctgacat tcgcagtgct    480
actttgacag gcactgtcga tttgggaagc tgcaacgagg gatgggagaa gtgcgcatct    540
ttctacacca tcctcgcgga ttgctgcagg aggccaaggg gctaa                   585
```

<210> SEQ ID NO 2
<211> LENGTH: 330
<212> TYPE: DNA
<213> ORGANISM: Allium Fistulosum

<400> SEQUENCE: 2

```
agaaacgtat tggtgaacaa cgaaggactg tacgcaggcc aatccctagt cgtagaacag     60
tacactttta caatgcagga tgactgcaac cttgtactct acgaatactg cgccccaatc    120
tgggcctcaa acacgggcgt caccggcaaa aatgggtgca gggccgtgat gcaggctgat    180
ggcaactttg tggtctacga tgttaacggg cgtgccgtct gggccagtaa cagcagaaga    240
gggaacggaa actatatcct ggtgcttcag gaggacagga acgttgttat ttacggatct    300
gatatttggt ctactggtac gtacagaaga                                     330
```

<210> SEQ ID NO 3
<211> LENGTH: 194
<212> TYPE: PRT
<213> ORGANISM: Allium Fistulosum

<400> SEQUENCE: 3

```
Met Asp Ser Thr Pro Ser Pro Lys Leu Met Ser Met Thr Thr Val Ala
 1               5                  10                  15

Thr Ile Leu Thr Ile Leu Ala Ser Thr Cys Met Ala Arg Asn Val Leu
            20                  25                  30

Val Asn Asn Glu Gly Leu Tyr Ala Gly Gln Ser Leu Val Val Glu Gln
        35                  40                  45

Tyr Thr Phe Thr Met Gln Asp Asp Cys Asn Leu Val Leu Tyr Glu Tyr
    50                  55                  60

Cys Ala Pro Ile Trp Ala Ser Asn Thr Gly Val Thr Gly Lys Asn Gly
65                  70                  75                  80

Cys Arg Ala Val Met Gln Ala Asp Gly Asn Phe Val Val Tyr Asp Val
                85                  90                  95

Asn Gly Arg Ala Val Trp Ala Ser Asn Ser Arg Arg Gly Asn Gly Asn
            100                 105                 110
```

```
Tyr Ile Leu Val Leu Gln Glu Asp Arg Asn Val Val Ile Tyr Gly Ser
            115                 120                 125

Asp Ile Trp Ser Thr Gly Thr Tyr Arg Arg Gly Pro Gly Pro Gly Pro
130                 135                 140

Gly Ala Ala Cys Lys Cys Asp Asp Gly Pro Asp Ile Arg Ser Ala
145                 150                 155                 160

Thr Leu Thr Gly Thr Val Asp Leu Gly Ser Cys Asn Glu Gly Trp Glu
                165                 170                 175

Lys Cys Ala Ser Phe Tyr Thr Ile Leu Ala Asp Cys Cys Arg Arg Pro
                180                 185                 190

Arg Gly
```

\<210\> SEQ ID NO 4
\<211\> LENGTH: 110
\<212\> TYPE: PRT
\<213\> ORGANISM: Allium Fistulosum

\<400\> SEQUENCE: 4

```
Arg Asn Val Leu Val Asn Asn Glu Gly Leu Tyr Ala Gly Gln Ser Leu
1               5                   10                  15

Val Val Glu Gln Tyr Thr Phe Thr Met Gln Asp Cys Asn Leu Val
            20                  25                  30

Leu Tyr Glu Tyr Cys Ala Pro Ile Trp Ala Ser Asn Thr Gly Val Thr
                35                  40                  45

Gly Lys Asn Gly Cys Arg Ala Val Met Gln Ala Asp Gly Asn Phe Val
        50                  55                  60

Val Tyr Asp Val Asn Gly Arg Ala Val Trp Ala Ser Asn Ser Arg Arg
65                  70                  75                  80

Gly Asn Gly Asn Tyr Ile Leu Val Leu Gln Glu Asp Arg Asn Val Val
                85                  90                  95

Ile Tyr Gly Ser Asp Ile Trp Ser Thr Gly Thr Tyr Arg Arg
                100                 105                 110
```

\<210\> SEQ ID NO 5
\<211\> LENGTH: 25
\<212\> TYPE: DNA
\<213\> ORGANISM: Artificial Sequence
\<220\> FEATURE:
\<223\> OTHER INFORMATION: A synthetic primer

\<400\> SEQUENCE: 5 atggacagta ctccatctcc taaac                                   25

\<210\> SEQ ID NO 6
\<211\> LENGTH: 21
\<212\> TYPE: DNA
\<213\> ORGANISM: Artificial Sequence
\<220\> FEATURE:
\<223\> OTHER INFORMATION: A synthetic primer

\<400\> SEQUENCE: 6 ttagcccctt ggcctcctgc a                                       21

\<210\> SEQ ID NO 7
\<211\> LENGTH: 22
\<212\> TYPE: DNA
\<213\> ORGANISM: Artificial Sequence
\<220\> FEATURE:
\<223\> OTHER INFORMATION: A synthetic primer

\<400\> SEQUENCE: 7 agaaacgtat tggtgaacaa cg                                                    22

<210> SEQ ID NO 8
<211> LENGTH: 25
<212> TYPE: DNA
<213> ORGANISM: Artificial Sequence
<220> FEATURE:
<223> OTHER INFORMATION: A synthetic primer

<400> SEQUENCE: 8
ttatcttctg taggtaccag tagac                                                 25

<210> SEQ ID NO 9
<211> LENGTH: 18
<212> TYPE: DNA
<213> ORGANISM: Artificial Sequence
<220> FEATURE:
<223> OTHER INFORMATION: A synthetic primer

<400> SEQUENCE: 9
gccccttggc ctcctgca                                                         18

<210> SEQ ID NO 10
<211> LENGTH: 9
<212> TYPE: PRT
<213> ORGANISM: Artificial Sequence
<220> FEATURE:
<223> OTHER INFORMATION: A synthetic peptide
<221> NAME/KEY: SITE
<222> LOCATION: 2,4,6,8
<223> OTHER INFORMATION: Xaa = any amino acid

<400> SEQUENCE: 10

Gln Xaa Asp Xaa Asn Xaa Val Xaa Tyr
 1               5

<210> SEQ ID NO 11
<211> LENGTH: 19
<212> TYPE: DNA
<213> ORGANISM: Artificial Sequence
<220> FEATURE:
<223> OTHER INFORMATION: A synthetic primer
<221> NAME/KEY: misc_feature
<222> LOCATION: 6
<223> OTHER INFORMATION: n = A or G
<221> NAME/KEY: misc_feature
<222> LOCATION: 7
<223> OTHER INFORMATION: n = C or G
<221> NAME/KEY: misc_feature
<222> LOCATION: 9
<223> OTHER INFORMATION: n = G or T

<400> SEQUENCE: 11
atgcannang actgcaacc                                                        19

<210> SEQ ID NO 12
<211> LENGTH: 173
<212> TYPE: PRT
<213> ORGANISM: Allium Fistulosum

<400> SEQUENCE: 12

Met Ala Tyr Ser Val Thr Cys Lys Leu Ile Met Val Cys Thr Val Gly
 1               5                  10                  15

Ala Ile Leu Ser Val Leu Thr Ala Thr Cys Met Gly Arg Asn Ile Leu
            20                  25                  30

Leu Asn Gly Glu Gly Leu Tyr Ala Gly Gln Ser Leu Glu Glu Gly Pro

```
                35                  40                  45
Tyr Arg Leu Ala Met Gln Asp Asp Cys Asn Leu Val Leu Tyr Asp Glu
 50                  55                  60

Tyr Ser Arg Pro Val Trp Ala Ser Asn Thr Gly Val Thr Gly Arg Asn
 65                  70                  75                  80

Gly Cys Arg Ala Val Met Gln Ala Asp Gly Asn Phe Val Val Tyr Asp
                 85                  90                  95

Ser Asn Ser Arg Ala Val Trp Ala Ser Asn Ser Arg Lys Gly Asn Gly
                100                 105                 110

Asn Tyr Ile Leu Val Leu Gln Lys Asp Arg Asn Ala Val Ile Tyr Gly
                115                 120                 125

Ser Asp Ile Trp Ser Thr Gly Thr Tyr Arg Arg Gly Val Gly Gly Ser
    130                 135                 140

Val Val Thr Ala Met Asn Gly Thr Val Asp Ala Gly Phe Ala Val Lys
145                 150                 155                 160

Asn Val Thr Thr Ala Ala Val Gly Asp Val Ala Ile Ala
                165                 170

<210> SEQ ID NO 13
<211> LENGTH: 166
<212> TYPE: PRT
<213> ORGANISM: Allium Fistulosum

<400> SEQUENCE: 13

Met Ala Ile Ser Val Asn Cys Lys Ile Ile Met Val Cys Ala Val Gly
  1               5                  10                  15

Thr Ile Leu Ser Ile Leu Thr Pro Thr Ser Met Gly Arg Asn Ile Leu
                 20                  25                  30

Leu Asn Gly Glu Gly Leu Tyr Ala Gly Gln Ser Leu Glu Glu Gly Ser
                 35                  40                  45

Tyr Lys Leu Ile Met Gln Asp Asp Cys Asn Leu Val Leu Phe Glu Tyr
 50                  55                  60

Ser Thr Gln Val Trp Ala Ser Asn Thr Gly Val Ser Gly Arg Asn Gly
 65                  70                  75                  80

Cys Arg Ala Val Met Gln Ala Asp Gly Asn Phe Val Val Tyr Asp Ser
                 85                  90                  95

Asn Ser Arg Ala Val Trp Ala Ser Gln Ser Arg Arg Gly Asn Gly Asn
                100                 105                 110

Tyr Ile Leu Ala Leu Gln Glu Asp Arg Asn Val Val Ile Tyr Gly Thr
                115                 120                 125

Asp Ile Trp Ser Thr Gly Thr Tyr Arg Arg Gly Val Gly Gly Thr Val
    130                 135                 140

Val Thr Val Ile Asn Gly Thr Val Asp Ala Gly Ser Gly Met Glu Asn
145                 150                 155                 160

Val Thr Ala Thr Ala Ala
                165

<210> SEQ ID NO 14
<211> LENGTH: 109
<212> TYPE: PRT
<213> ORGANISM: Allium Fistulosum

<400> SEQUENCE: 14

Arg Asn Ile Leu Thr Asn Asp Glu Gly Leu Tyr Ala Gly Gln Ser Leu
  1               5                  10                  15

Asp Val Asn Pro Tyr His Leu Ile Met Gln Glu Asp Cys Asn Leu Val
```

```
                20                  25                  30
Leu Tyr Asp His Ser Thr Ala Val Trp Ser Ser Asn Thr Asp Ile Pro
                35                  40                  45
Gly Lys Lys Gly Cys Lys Ala Val Leu Gln Ser Asp Gly Asn Phe Val
            50                  55                  60
Val Tyr Asp Ala Glu Gly Ala Ser Leu Trp Ala Ser His Ser Val Arg
 65                  70                  75                  80
Gly Asn Gly Asn Tyr Val Leu Val Leu Gln Glu Asp Gly Asn Val Val
                85                  90                  95
Ile Tyr Gly Ser Asp Ile Trp Ser Thr Asn Thr Tyr Lys
            100                 105

<210> SEQ ID NO 15
<211> LENGTH: 181
<212> TYPE: PRT
<213> ORGANISM: Allium Fistulosum

<400> SEQUENCE: 15

Met Gly Arg Thr Thr Ser Ser Pro Lys Ala Met Met Arg Ile Ala Thr
  1               5                  10                  15
Val Ala Ala Ile Leu Thr Ile Leu Ala Ser Thr Cys Met Ala Arg Asn
                20                  25                  30
Val Leu Thr Asn Gly Glu Gly Leu Tyr Ala Gly Gln Ser Leu Asp Val
                35                  40                  45
Glu Gln Tyr Lys Phe Ile Met Gln Asp Asp Cys Asn Leu Val Leu Tyr
            50                  55                  60
Glu Tyr Ser Thr Pro Ile Trp Ala Ser Asn Thr Gly Val Thr Gly Lys
 65                  70                  75                  80
Asn Gly Cys Arg Ala Val Met Gln Arg Asp Gly Asn Phe Val Val Tyr
                85                  90                  95
Asp Val Asn Gly Arg Pro Val Trp Ala Ser Asn Ser Val Arg Gly Asn
                100                 105                 110
Gly Asn Tyr Ile Leu Val Leu Gln Lys Asp Arg Asn Val Val Ile Tyr
            115                 120                 125
Gly Ser Asp Ile Trp Ser Thr Gly Thr Tyr Arg Arg Ser Val Gly Gly
            130                 135                 140
Ala Val Val Met Ala Met Asn Gly Thr Val Asp Gly Gly Ser Val Ile
145                 150                 155                 160
Gly Pro Val Val Asn Gln Asn Val Thr Ala Ala Ile Arg Lys Val
                165                 170                 175
Gly Thr Gly Ala Ala
            180

<210> SEQ ID NO 16
<211> LENGTH: 180
<212> TYPE: PRT
<213> ORGANISM: Allium Fistulosum

<400> SEQUENCE: 16

Met Gly Arg Thr Thr Pro Ser Pro Lys Leu Ile Met Ser Ile Thr Thr
  1               5                  10                  15
Val Ala Ala Ile Leu Thr Ile Leu Ala Ser Thr Cys Met Ala Arg Asn
                20                  25                  30
Leu Leu Thr Asn Gly Glu Gly Leu Tyr Ala Gly Gln Ser Leu Asp Val
                35                  40                  45
Glu Gln Tyr Lys Phe Ile Met Gln Asp Asp Cys Asn Leu Val Leu Tyr
```

```
            50                 55                 60
Glu Tyr Ser Thr Pro Ile Trp Ala Ser Asn Thr Gly Val Thr Gly Lys
65                  70                  75                  80

Asn Gly Cys Arg Ala Val Met Gln Lys Asp Gly Asn Phe Val Val Tyr
                85                  90                  95

Asp Val Asn Gly Arg Pro Val Trp Ala Thr Asn Ser Val Arg Gly Asn
                100                 105                 110

Gly Asn Tyr Ile Leu Val Leu Gln Gln Asp Arg Asn Val Val Ile Tyr
            115                 120                 125

Gly Ser Asp Ile Trp Ser Thr Gly Thr Tyr Arg Arg Ser Ala Gly Gly
            130                 135                 140

Pro Val Val Met Ala Met Asn Gly Thr Val Asn Gly Gly Ser Val Val
145                 150                 155                 160

Gly Pro Val Ile Val Asn Gln Asn Val Thr Ala Ile Arg Lys Val Gly
                165                 170                 175

Thr Ser Ala Ala
            180

<210> SEQ ID NO 17
<211> LENGTH: 164
<212> TYPE: PRT
<213> ORGANISM: Allium Fistulosum

<400> SEQUENCE: 17

Thr Val Ala Thr Ile Leu Thr Ile Leu Ala Ser Thr Cys Met Ala Arg
1               5                   10                  15

Asn Val Leu Val Asn Asn Glu Gly Leu Tyr Ala Gly Gln Ser Leu Val
                20                  25                  30

Val Glu Gln Tyr Thr Phe Ile Met Gln Asp Asp Cys Asn Leu Val Leu
            35                  40                  45

Tyr Glu Tyr Ser Thr Pro Ile Trp Ala Ser Asn Thr Gly Val Thr Gly
        50                  55                  60

Lys Asn Gly Cys Arg Ala Val Met Gln Ala Asp Gly Asn Phe Val Val
65                  70                  75                  80

Tyr Asp Val Lys Gly Arg Ala Val Trp Ala Ser Asn Ser Arg Arg Gly
                85                  90                  95

Asn Gly Asn Tyr Ile Leu Val Leu Gln Lys Asp Arg Asn Val Val Ile
            100                 105                 110

Tyr Gly Ser Asp Ile Trp Ser Thr Gly Thr Tyr Arg Lys Lys Val Gly
            115                 120                 125

Gly Thr Val Val Met Ala Met Asn Gly Thr Val Asp Gly Gly Ser Val
            130                 135                 140

Val Gly Pro Val Thr Val Asn Gln Asn Val Thr Ala Val Arg Lys Val
145                 150                 155                 160

Ala Ala Ala Ala
```